(12) United States Patent
Knauf et al.

(10) Patent No.: US 10,280,135 B2
(45) Date of Patent: May 7, 2019

(54) METHOD FOR PRODUCING ISOCYANATES

(71) Applicant: Covestro Deutschland AG, Leverkusen (DE)

(72) Inventors: Thomas Knauf, Dormagen (DE); Dirk Manzel, Moers (DE); Peter Plathen, Krefeld (DE); Stefan Wershofen, Mönchengladbach (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/762,227

(22) PCT Filed: Sep. 28, 2016

(86) PCT No.: PCT/EP2016/073036
§ 371 (c)(1),
(2) Date: Mar. 22, 2018

(87) PCT Pub. No.: WO2017/055311
PCT Pub. Date: Apr. 6, 2017

(65) Prior Publication Data
US 2018/0265457 A1  Sep. 20, 2018

(30) Foreign Application Priority Data

Sep. 30, 2015 (EP) .................................... 15187592

(51) Int. Cl.
*C07C 263/10* (2006.01)

(52) U.S. Cl.
CPC .................. *C07C 263/10* (2013.01)

(58) Field of Classification Search
CPC ........................ C07C 263/10; C07C 265/14
See application file for complete search history.

(56) References Cited

U.S. PATENT DOCUMENTS

| | | | |
|---|---|---|---|
| 4,422,976 A | 12/1983 | Yamamoto et al. | |
| 4,764,308 A | 8/1988 | Sauer et al. | |
| 4,851,570 A | 7/1989 | Zaby et al. | |
| 5,599,968 A | 2/1997 | Bankwitz et al. | |
| 6,803,482 B2 | 10/2004 | Jenne et al. | |
| 6,803,483 B2 | 10/2004 | Lokum et al. | |
| 6,930,199 B2 | 8/2005 | Meyn et al. | |
| 6,974,880 B2 | 12/2005 | Biskup et al. | |
| 7,038,002 B2 | 5/2006 | Pirkl et al. | |
| 7,084,297 B2 | 8/2006 | Woelfert et al. | |
| 7,108,770 B2 | 9/2006 | Gruen et al. | |
| 7,118,653 B2 | 10/2006 | Brady et al. | |
| 7,442,835 B2 | 10/2008 | Keggenhoff et al. | |
| 7,541,487 B2 | 6/2009 | Pohl et al. | |
| 7,547,801 B2 | 6/2009 | Pohl et al. | |
| 7,584,629 B2 | 9/2009 | Sohn et al. | |
| 7,615,662 B2 | 11/2009 | Pohl et al. | |
| 7,645,900 B2 | 1/2010 | Lorenz et al. | |
| 7,754,915 B2 | 7/2010 | Herold et al. | |
| 8,079,752 B2 | 12/2011 | Rausch et al. | |
| 8,097,751 B2 | 1/2012 | Koch et al. | |
| 8,153,838 B2 | 4/2012 | Bulan et al. | |
| 8,563,768 B2 | 10/2013 | Bruns et al. | |
| 8,829,232 B2 | 9/2014 | Penzel et al. | |
| 9,024,057 B2 | 5/2015 | Pohl et al. | |
| 9,498,757 B2 | 11/2016 | Grob et al. | |
| 2007/0261437 A1 | 11/2007 | Boonstra et al. | |
| 2010/0298596 A1 | 11/2010 | Keggenhoff et al. | |
| 2013/0060062 A1* | 3/2013 | Mattke .................. C07C 263/10 560/347 |
| 2015/0018575 A1 | 1/2015 | Gillis et al. | |

FOREIGN PATENT DOCUMENTS

| | | |
|---|---|---|
| CN | 102527312 A | 7/2012 |
| WO | 2013029918 A1 | 3/2013 |
| WO | 2013060836 A1 | 5/2013 |

OTHER PUBLICATIONS

W. Siefken, Liebigs Ann. 562, 75-106 (1949).
Ullmanns Encyklopädie der technischen Chemie [Ullmann's Encyclopedia of Industrial Chemistry], 4th ed. (1977), vol. 13, p. 351 to 353.
G. Wegener et al. Applied Catalysis A: General 221 (2001), p. 303-335, Elsevier Science B.V.
"Droplet Separation", A. Bürkholz, VCH Verlagsgesellschaft, Weinheim—New York—Basle—Cambridge, 1989, pp. 47-51, 75-77, 99-102, 123-125, 141, 146-154, 191-192, 201-209.

* cited by examiner

*Primary Examiner* — Jafar F Parsa
*Assistant Examiner* — Blaine G Doletski
(74) *Attorney, Agent, or Firm* — Donald R. Palladino; N. Denise Brown

(57) ABSTRACT

The invention relates to a continuously operated method for producing isocyanates by reacting the corresponding amines with phosgene. When changing the target production capacity starting from a starting state with a specified production capacity and ending with an end state with a different production capacity, the current excess phosgene at the time of the transition period between the starting state and the end state, the change of the amine mass flow beginning during said time, is at least equal to and preferably greater than the excess phosgene during the production period when the production capacity is in the starting state prior to the beginning of the transition period; and the average excess phosgene during the transition period is greater than the excess phosgene during the production period when the production capacity is in the starting state prior to the beginning of the transition period.

16 Claims, 4 Drawing Sheets

METHOD FOR PRODUCING ISOCYANATES

CROSS-REFERENCE TO RELATED APPLICATIONS

This application is a national stage application under 35 U.S.C. § 371 of PCT/EP2016/073036, filed Sep. 28, 2016, which claims the benefit of European Application No. 15187592.9, filed Sep. 30, 2015, both of which are being incorporated by reference herein.

FIELD

The invention relates to a continuous process for preparing isocyanates by reacting the corresponding amines with phosgene, in which, in the event of an alteration in the target production capacity proceeding from a starting state with a particular production capacity and ending in a final state with a different production capacity, in the transition period between the starting and final states, the instantaneous phosgene excess at the point in time in the transition period at which the alteration of the amine mass flow rate is commenced is at least as high as and preferably greater than the phosgene excess during the period of production with the production capacity in the starting state prior to commencement of the transition period, and the average phosgene excess during the transition period is greater than the phosgene excess during the period of production with the production capacity in the starting state prior to commencement of the transition period.

BACKGROUND

Isocyanates are produced in large volumes and serve mainly as starting materials for production of polyurethanes. They are usually prepared by reacting the corresponding amines with phosgene, using phosgene in a stoichiometric excess. The reaction of the amines with the phosgene can be effected either in the gas phase or in the liquid phase, wherein the reaction can be conducted batchwise or continuously (W. Siefken, Liebigs Ann. 562, 75-106 (1949)). There have already been multiple descriptions of processes for preparing organic isocyanates from primary amines and phosgene; see, for example, Ullmanns Encyklopadie der technischen Chemie [Ullmann's Encyclopedia of Industrial Chemistry], 4th ed. (1977), volume 13, p. 351 to 353, and G. Wegener et al. Applied Catalysis A: General 221 (2001), p. 303-335, Elsevier Science B. V. There is global use both of aromatic isocyanates, for example methylene diphenyl diisocyanate (MMDI—"monomeric MDI"), polymethylene polyphenylene polyisocyanate (a mixture of MMDI and higher homologs, PMDI, "polymeric MDI") or tolylene diisocyanate (TDI), and of aliphatic isocyanates, for example hexamethylene diisocyanate (HDI) or isophorone diisocyanate (IPDI).

A distinction is generally drawn between two ways of conducting the process, namely reaction in the gas phase and reaction in the liquid phase.

It is a feature of the process regime in the gas phase, typically referred to as gas phase phosgenation, that the reaction conditions are chosen such that usually the amine, isocyanate and phosgene reaction components, but preferably all the reactants, products and reaction intermediates, are gaseous under the conditions chosen.

It is a feature of the process regime in the liquid phase, typically referred to as liquid phase phosgenation, that the reaction conditions are chosen such that at least the amine, crude isocyanate and phosgene reaction components, but preferably all the reactants, products and reaction intermediates, are in liquid form under the conditions chosen (which in this connection also includes the state of a gas physically dissolved in the liquid phase) in a suitable solvent and the solvent is separated from the crude isocyanate and recycled into the reaction circuit in purified or else unpurified form.

For the mixing of the amine with the phosgene in liquid phase phosgenation, it is possible to use a dynamic or static mixer; in gas phase phosgenation, the use of a mixing nozzle is advisable. An important factor is rapid and good mixing of the feedstocks, since the isocyanate formed, in the case of poor mixing of the feedstocks, reacts with amine which is then present in a local excess to give urea or other troublesome by-products of high viscosity or in solid form. This gives rise to caking of equipment and blockages (for example in the pipelines) which lead to unwanted cleaning outages and hence to poorer service lives of the plant, i.e. to suboptimal economic viability. Consequently, the focus in the isocyanate-preparing industry in the recent past was on the optimization of the mixing of the feedstocks, as can also be inferred from the multitude of publications. The following patent applications are cited here by way of example: CN 102527312 A, WO 2013/048873 A1, WO 2013/060836 A1, EP 2 077 150 A1, EP-A-1 555 258, WO 2006/108740 A1, WO 2010/015667 A1, or EP-A-1 526 129.

Modern industrial scale preparation of polyisocyanates is continuous, and the reaction is conducted as an adiabatic phosgenation as described, for example, in EP 1 616 857 A1. Unwanted deposits and by-products in the reactor are avoided through correct choice of reaction temperature and pressure. In the mixing space, a molar excess of phosgene relative to the primary amino groups should be ensured. A three-stage phosgenation line is described in EP 1 873 142 A1, in which the pressure between the first stage of a mixer and the second stage of a first phosgenation reactor remains the same or rises and, in the third stage, an apparatus for phosgene removal, the pressure is lower than in the second stage.

WO 2013/029918 A1 (WO '918 from now on) describes a process for preparing isocyanates by reacting the corresponding isocyanates with phosgene, which can be conducted at different loads on the plant without any problems. More particularly, in the case of operation of the plant within the partial load range as well, the mixing and/or the reaction is to be effected within the dwell time window optimized in each case, by increasing the ratio of phosgene to amine or adding one or more inert substances to the phosgene and/or amine stream. The process of the invention is to enable operation of an existing plant at different loads with constant product and process quality. The intention is to dispense with the provision of several plants with different nameplate capacities. The following findings are made: both in the gas phase phosgenation and in the liquid phase phosgenation, the mixing of the reactants and the dwell time of the reaction mixture in the corresponding reaction spaces are critical reaction parameters. The plans for preparation of isocyanates by phosgenation of amines therefore have to be matched to the specific demands with respect to rapid mixing of the reactant streams and narrow dwell time windows. Plans for phosgenation of amines are designed here essentially for the maximum flow rates or the respective nameplate capacity. This means that both mixing elements, such as nozzles, and the reaction spaces, for example dwell time reactors, at the nameplate capacity, work within the optimal range with optimized yield, purity of the products, etc. However, if the plant is not at full load, meaning that it is being operated only at a fraction of the nameplate capacity, there will be a change, for example, in the dwell times, and the plant as a result is no longer working within the optimal range. This is the case, for example, in startup and shutdown operations, at partial load of the plant and in the event of faults in the plant. In these cases of reduced production capacity, both the mixing elements and the dwell time reactors are not working within the optimal range. The consequences are yield losses, problems with caking in equipment and/or losses of quality. In order to avoid the aforementioned problems, WO '918 suggests that sufficiently rapid mixing of the reactants should be ensured. Methods of implementing short mixing times are known in principle. In the mixing units, it is possible to use mixing aggregates having dynamic or static mixers. Preference is given to using one or more static mixing elements in the mixing units. Suitable static mixing elements include, for example, nozzles, smooth jet nozzles or Venturi nozzles that are known from combustion technology, and Laval nozzles. WO '918 suggests, as a particularly advantageous execution of a static mixing element, a mixing element as described in WO 2010/015667 A1. Dynamic mixers used may, for example, be rotor/stator systems disposed in the mixing units. According to WO '918, preference is given to using static mixing elements, especially nozzles. However, the process according to WO '918 solves these problems (yield losses, fouling problems and/or losses of quality) at the cost of use of elevated amounts of solvent and/or of elevated amounts of phosgene and not through the use of suitable nozzles. This means that, under partial load of the plant, the dwell time in the reactors and apparatuses in the plant is kept the same or nearly the same compared to the operation of the plant as intended at nameplate capacity. This gives rise to serious drawbacks, for example a higher specific and possibly absolute phosgene holdup or use of an elevated amount of solvent under partial production load. This is of course associated with the higher energy expenditure for the workup of the crude isocyanate, where more solvent than necessary has to be distilled and more phosgene than necessary recovered, i.e. condensed. As a result, the economic viability of the process suffers in addition to the load already being low.

The problems of optimal mode of operation at different load states that are discussed in WO '918 gives reason for some fundamental considerations:

The operating of a production plant both in the region of nameplate capacity (also referred to as "nameplate load") and in the region of reduced production capacity (also referred to as "partial load range") should each be considered to be a steady state in that the flow rates of reactants (amine, phosgene, optionally diluent), once set, remain constant. In order to change from a steady state (for example production at nameplate capacity) to a different steady state (for example production at 75% of nameplate capacity), however, a transition state is inevitably passed through each time, in which the flow rates of reactants are subject to constant changes, at the end of which the new steady state is established. In such transition states, the flow rates are therefore changing, either continuously or within discrete intervals. WO '918 does not discuss the configuration of such transition states in detail. Instead, WO '918 is concerned merely with the optimal operating of the process in the steady states before and after a transition state.

Published specification DE 10 2009 032413 A1 is concerned with a process for preparing isocyanates in the gas phase, in which the phosgene recovery yield is increased by means of a particular process regime in the workup of the gas stream comprising hydrogen chloride and phosgene which forms in the phosgenation. This document is not concerned with transition states between two operating states with different load either.

Patent application WO 03/045900 A1 is based on the objective of providing a process for preparing isocyanates by phosgenation in the gas phase, by means of which both a high heat exchange area and, even though it is impossible to completely avoid formation of solids, a very long operating life of the production plant, especially a production plant on the industrial scale, is to be achieved. For this purpose, it is suggested that the reaction be conducted in a non-cylindrical reaction channel. This document is not concerned with transition states between two operating states with different load either.

Published specification DE 32 12 510 A1 describes a two-stage liquid phase process for preparing an organic isocyanate. This document is not concerned with transition states between two operating states with different load either.

SUMMARY

There was therefore a need for further improvements in the preparation of isocyanates. More particularly, there was a need for a further process for preparing isocyanates by reacting the corresponding amines with phosgene, which can be conducted under different loads without the drawbacks described above, and which, in the event of an actual change in load in the non-steady-state phase, can be run in such a way that there is no caking and precipitation in the equipment and the production plant used, even after multiple changes in load, can be operated seamlessly and with good product quality over a long period. In the operation of the production plant in the steady-state phases (nameplate capacity or partial load range), the ratio of phosgene to amine and also the concentration of the phosgene and amine feedstocks in solvents and inert gases are to be kept the same and the mixing and/or reaction are to be effected within the dwell time window that results therefrom.

Taking account of this need, the present invention provides a continuous process for preparing an isocyanate (1) with a target production capacity of isocyanate (1), expressed as the mass flow rate, of $m_{1,\,target}$, with at least one change in the target production capacity $m_{1,\,target}$ (a so-called "change in load"), comprising the reaction of the amine (2) corresponding to the isocyanate (1) with phosgene (3) in a reaction space, in which (i) the amine (2) is fed to the reaction space with a mass flow rate $m_2$ and phosgene (3) to the reaction space with a mass flow rate $m_3$, wherein (ii) $m_2$ and $m_3$ are always chosen such that phosgene (3) is present in excess relative to the primary amino groups of the amine (2), wherein (iii) in the at least one change in the target production capacity $m_{1,\,target}$, which is conducted from a starting state $m_{1,\,target}(A) \neq 0$ with a corresponding amine mass flow rate $m_{2,\,target}(A)$ and a phosgene mass flow rate $m_{3,\,target}(A)$ selected with regard to (ii) to a final state $m_{1,\,target}(E) \neq 0$ with a corresponding amine mass flow rate $m_{2,\,target}(E)$ and a phosgene mass flow rate $m_{3,\,target}(E)$ selected with regard to (ii), the mass flow rates of amine (2) $m_2$ and phosgene (3) $m_3$ are altered during the transition period between the starting state and final state in such a way that (iii-1) the instantaneous phosgene excess at the point in time in the transition period at which the alteration of the mass flow rate $m_2$ from $m_{2,\,target}(A)$ to $m_{2,\,target}(E)$ is commenced is at least as high as and preferably greater than the phosgene excess during the period of production with the production capacity $m_{1,\ target}$ (A) prior to commencement of the transition period, and that (iii-2) the average phosgene excess during the transition period is greater than the phosgene excess during the period of production with the production capacity $m_{1,\ target}$ (A) prior to commencement of the transition period.

The present invention is concerned with changes in the target production capacity (i.e. $m_{1,\ target}$ (A)≠$m_{1,\ target}$ (E)) during continuous operation, i.e. proceeding from a particular state of production of the isocyanate (1) (i.e. $m_{1,\ target}$ (A)≠0) and ending in another state of production of the isocyanate (1) ($m_{1,\ target}$ (E)≠0). In other words: the process of the invention, in all embodiments, encompasses at least one change (one alteration) in the target production capacity (i.e. $m_{1,\ target}$ (A)≠$m_{1,\ target}$ (E)), more particularly a change in the target production capacity by a value in the range from 10% to 90%, more preferably in the range from 20% to 80%, most preferably in the range from 30% to 70%, based in each case on the starting value $m_{1,\ target}$ (A). Given a starting value of $m_{1,\ target}$ (A) of, for example, 150 kg/h, accordingly, an alteration in the target production capacity by 30% based on $m_{1,\ target}$ (A) corresponds either to a lowering from $m_{1,\ target}$ target to 105 kg/h or a rise in $m_{1,\ target}$ to 195 kg/h. Such alterations in the production capacity are also referred to as a change in load. Changes in load in this context should be distinguished from startup and shutdown operations in which a production plant not in operation (i.e. $m_{1,\ target}$ (A)=0) is put into operation (i.e. $m_{1,\ target}$ (E)≠0) or a production plant in operation (i.e. $m_{1,\ target}$ (A)≠0) is taken out of operation (i.e. $m_{1,\ target}$ (E)=0). The present invention is thus concerned with the procedure that should advantageously be run between the two steady states before and after the change in load, i.e. in the transition period between the starting state and final state. In other words: processes in which isocyanate (1) is constantly being produced with the same target production capacity $m_{1,\ target}$—within variations that are customary in operation of ±2.5%, preferably ±1.0% of the target value—and in which the instantaneous production capacity $m_1$ (inevitably) deviates from this target production capacity only in the course of startup (period between $m_1$=0 and $m_1$=$m_{1,\ target}$) and in the course of shutdown (period between $m_1$=$m_{1,\ target}$ and $m_1$=0), meaning that there is no transition period at all in the sense described above, do not form part of the subject matter of the present invention.

In the reaction space, the phosgenation of the amine (2) to the corresponding isocyanate (1) takes place. The reaction space begins where amine (2) and phosgene (3) encounter one another for the first time. This may be within a mixing device connected upstream of a dwell time device for completing the conversion. In this case, the mixing device and dwell time device together form the reaction space.

DETAILED DESCRIPTION

Figure 1:
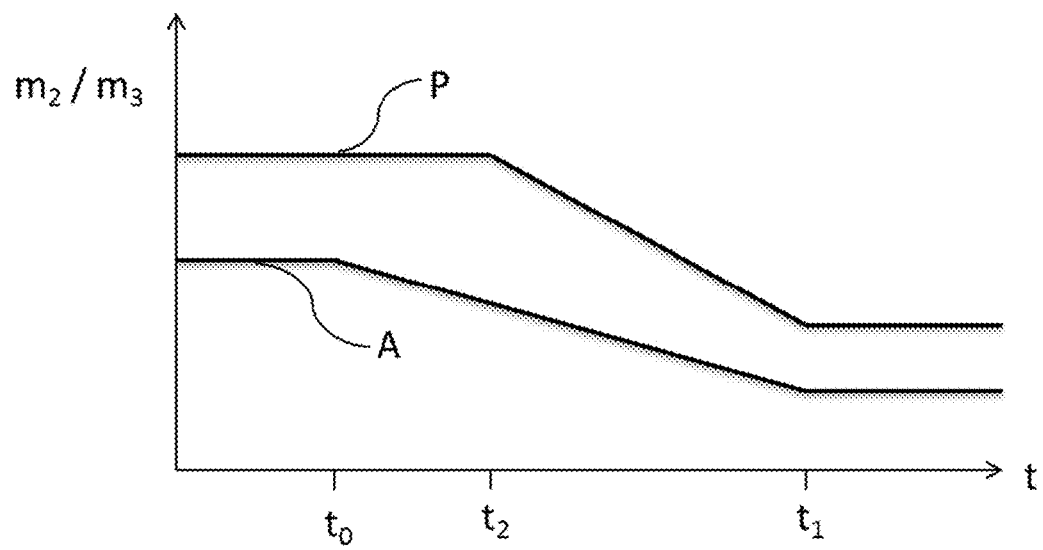
FIG. 1 is a graph of the mass flow rates of phosgene and amine against time in the process of the invention over the transition period in which the production capacity is being reduced.

The isocyanate (1) to be prepared is produced with a target production capacity $m_{1,\ target}$ (reported as the mass flow rate, i.e. as "mass of isocyanate prepared per unit time", for example in kg of isocyanate per hour). The target production capacity is variable within the technical limits fixed by the boundary conditions (for example the size of the apparatus available) in an existing production plant and is adjusted depending on the market demands. This target production capacity corresponds to an amine mass flow rate $m_{2,\ target}$ (likewise reported as mass flow rate, for example in kg of amine per hour), which is calculated under the assumption of 100% yield from the target production capacity. The target phosgene mass flow rate $m_{3,\ target}$ (likewise reported as mass flow rate, for example in kg of phosgene per hour) is always chosen such that phosgene is in excess relative to the primary amino groups of the amine (2). In theoretical terms, one mole of phosgene reacts with one mole of primary amino groups to give one mole of isocyanate groups. For example, accordingly, in the case of a diamine as amine (2) to be phosgenated, more than two moles of phosgene are used per mole of diamine. The amount of phosgene used in addition relative to the amount of phosgene theoretically required is referred to as phosgene excess. In the context of the present invention, the mass flow rates $m_2$ and $m_3$ each relate to amine (2) and phosgene (3) as such. If amine (2) and phosgene (3) are diluted with a solvent or inert gas to give a mixture (20) comprising amine (2) and a mixture (30) comprising phosgene (3) (which is preferred), it is of course the proportion of amine (2) and phosgene (3) present therein that is crucial for the determination of the phosgene excess.

The production of the isocyanate (1) at a particular target production capacity (for example at the nameplate capacity of the production plant) $m_{1,\ target}$t (A) is conducted for a period of time $t_A$ (starting state). During this period of time $t_A$, $m_2$=$m_{2,\ target}$ (A). The phosgene mass flow rate $m_3$ over this period of time $t_A$ is adjusted to a particular value $m_{3,\ target}$ (A).

The production capacity is now to be altered (for example to 75% of nameplate capacity [corresponding to a change, based on $m_{1,\ target}$ (A), by 25%] as a result of a fall in demand for the isocyanate produced). The new target state corresponds to the final state. The period of time of production in this new state is also referred to as $t_E$ in the discussion which follows. (Should another change in load be planned at a later point in time, this period of time $t_E$ would be regarded as $t_A$ "from the point of view of this new change in load". However, this is unimportant for the discussion; for reasons of simplification of the discussion, therefore, the starting point used hereinafter will therefore always be a change in load with a proceeding and a subsequent steady state over the periods of time $t_A$ and $t_E$.) Between the end of the starting state (in the example chosen, the end of production at nameplate capacity) and the attainment of the final state (in the example chosen, the attainment of production at 75% nameplate capacity), there is a transition period to $t_Ü$. This transition period $t_Ü$ begins at the point in time at which the mass flow rate $m_2$ and/or $m_3$ is for the first time increased or reduced from the target value $m_{2,\ target}$ (A) or $m_{3,\ target}$ (A) set in the respective case for the purpose of an alteration in the production capacity. This point in time is referred to hereinafter as $t_0$. If the change in the mass flow rates $m_2$ and $m_3$ from the target value $m_{2,\ target}$ (A) or $m_{3,\ target}$ (A) set in each case to the final target value in each case commences at different points in time, which is preferred, the point in time of commencement of that alteration in mass flow rate which is initiated earlier is referred to as to and the point in time of commencement of that alteration in mass flow rate which is initiated later as $t_2$ (cf. the figures as well). To the extent that deviations in the phosgene flow rate $m_3$ from $m_{3,\ target}$ (A) merely reflect variations (whether intended or unintended) in the phosgene excess over the period of time $t_A$, such changes do not mark the commencement of the transition period $t_Ü$. The transition period $t_Ü$ ends at the point in time at which the mass flow rates $m_2$ and $m_3$ have reached their respective target values $m_{2,\ target}$ (E) and $m_{3,\ target}$ (E). This point in time is referred to hereinafter as $t_1$.

A first feature essential to the invention is that the instantaneous phosgene excess at the point in time in the transition period at which the alteration of the mass flow rate $m_2$ from $m_{2,\ target}$ (A) to $m_{2,\ target}$ (E) is commenced is at least as high as and preferably greater than the phosgene excess during the period of production with the production capacity $m_{1,\ target}$ (A) prior to commencement of the transition period (feature (iii-1)). For a given amine, the phosgene excess can simply be calculated from the known values of the two mass flow rates $m_2$ and $m_3$. The phosgene excess over the period of time of production with production capacity $m_{1,\ target}$ (A) is thus found in a simple manner from the two flow rates $m_{2,\ target}$ (A) and $m_{3,\ target}$ (A). Should (in a non-preferable manner) the instantaneous phosgene mass flow rate $m_3$ be subject to variations during the period of time $t_A$ and should it, as a result, occasionally deviate significantly from the target value $m_{3,\ target}$ (A), for the purposes of setting the instantaneous phosgene excess at the point in time of the transition period at which the alteration in the mass flow rate $m_2$ from $m_{2,\ target}$ (A) to $m_{2,\ target}$ (E) is commenced, the phosgene excess during the period of time of production with production capacity $m_{1,\ target}$ (A) prior to commencement of the transition period which is determined using the average phosgene mass flow rate $m_3$ over the period of time $t_A$ is used as the basis.

A second feature essential to the invention is that the average phosgene excess during the transition period is greater than the phosgene excess during the period of production with the production capacity $m_{1,\ target}$ (A) prior to commencement of the transition period (feature (iii-2)). During the transition period $t_Ü$, the instantaneous phosgene excess is variable. This may be because $m_2$ and $m_3$ are increased or lowered for the first time at different points in time for the purpose of a change in load (cf. the drawings FIG. 1 to FIG. 4) and/or because there is a greater drop overall in the function $m_3(t)$ between $t_0$ and $t_1$ than in $m_2(t)$, as shown in schematic form in FIG. 1 and FIG. 2 and/or because there is a steeper rise overall in the function $m_3(t)$ between $t_0$ and $t_1$ than in $m_2(t)$, as shown in schematic form in FIG. 3 and FIG. 4. What is essential is that the average phosgene excess during the transition period (i.e. in the period of time $t_Ü$ commencing at $t_0$ and ending at $t_1$) is greater than the phosgene excess during the period of time of production with the production capacity $m_{1,\ target}$ (A) prior to commencement of the transition period. In relation to the latter, the statements made above with regard to feature (iii-1) are of course likewise applicable. The average phosgene excess during the transition period can thus be calculated in a simple manner, for example from the mass flow rates for phosgene and amine recorded in the process control system.

Particular embodiments of the invention are elucidated in detail hereinafter. Various embodiments can be combined with one another as desired, unless the opposite is apparent to the person skilled in the art from the context. As already mentioned at the outset, the present invention is concerned with alterations in the target production capacity during continuous operation, i.e. with changes in load. As is known to the person skilled in the art, a production plant for the preparation of isocyanates (1) is designed for a particular target nameplate capacity. Nameplate capacity refers here to the amount of target product produced per unit time in a chemical plant, for which the plant has been designed or dimensioned. This nameplate capacity in current plant sizes may be in the order of magnitude of several hundreds of thousands of metric tons of the target isocyanate (1) per annum. Operation at nameplate capacity therefore also sets the flow rates (amounts per unit time) that are used to achieve the nameplate capacity of a plant. In the preparation of isocyanates (1) from the corresponding amines (2) and phosgene (3), this means that a production plant is designed for the production of a particular amount of isocyanate within a particular period of time ($m_{1,\ target,\ nameplate}$), for which purpose particular mass flow rates of amine ($m_{2,\ target,\ nameplate}$) and phosgene ($m_{3,\ target,\ nameplate}$) have to be supplied to the reaction space. In the context of the invention, the term "below nameplate capacity" (or else "partial load") relates to the amine(s) (2) used; in other words, "operation below nameplate capacity" means that the flow rate $m_2$ of amine used is less than the flow rate of amine envisaged for operation at nameplate capacity of a production plant ($m_{2,\ target,\ nameplate}$).

The process of the invention is especially suitable for those changes in load in which the starting state or final state is in the range from
- the nameplate capacity of the production plant down to 20% of the nameplate capacity of the production plant,
- preferably from the nameplate capacity of the production plant down to 30% of the nameplate capacity of the production plant and
- more preferably from the nameplate capacity of the production plant down to 40% of the nameplate capacity of the production plant.

There is no upper limit to the periods of time within which the production plant can be operated below its nameplate capacity, such that a production plant can be operated below nameplate capacity by the process of the invention even over a prolonged period, meaning that the mass flow rate of the amine(s) $m_2$ used is continuously below the mass flow rate $m_{2,\ target,\ nameplate}$ of the amines used at nameplate capacity of the production plant used. It is also possible in accordance with the invention to switch back and forth between operation at nameplate capacity and operation below nameplate capacity in the case of employment of the measures envisaged in accordance with the invention. The process of the invention permits operation of an existing plant at different loads (different production capacities) with equal product and process quality, without accepting additional costs for the workup compared to production at nameplate capacity.

In addition, given correct setting of the process parameters, depending on the instantaneous production capacity (nameplate capacity, partial load or during a change in load), it is also possible to avoid deposition and caking problems in the equipment.

The present invention is applicable to the reaction of amines (2) with phosgene (3) to give isocyanates (1) both in the liquid phase and in the gas phase.

If the reaction is conducted in the liquid phase, in the steady-state operation before (i.e. in the period of time $t_A$) or after (i.e. in the period of time $t_E$) a change in load, preference is given to setting a phosgene excess corresponding to a molar ratio of phosgene to primary amino groups of 1.10:1 to 30.0:1, more preferably of 1.25:1 to 5.00:1.

If the reaction is conducted in the gas phase, in the steady-state operation before (i.e. in the period of time $t_A$) or after (i.e. in the period of time $t_E$) a change in load, preference is given to setting a molar ratio of phosgene to primary amino groups of 2.50:1 to 5.00:1, more preferably of 2.60:1 to 4.50:1 and most preferably of 2.70:1 to 4.00:1.

Irrespective of the process variant (liquid or gas phase phosgenation), the phosgene excess after the end of the transition period, provided that feature (ii) is observed, can be chosen freely; in other words, it is not absolutely necessary to set the same phosgene excess as before the change in load. Nevertheless, the latter variant is the preferred variant; in other words, the process is preferably operated such that the excess of phosgene during the production with the production capacity $m_{1,\ target}$ (A) before commencement of the transition period is equal to the phosgene excess during the production with the production capacity $m_{1,\ target}$ (E) after the end of the transition period.

The transition period $t_U$ (i.e. the duration of the change in load, the duration between the two steady states) is preferably at least 0.50 minute, more preferably at least 5.0 minutes and most preferably at least 15 minutes. The transition period is subject to a time limitation basically arising from the aim of operating the production plant in a steady state again as soon as possible. Preferably, the transition period is therefore not more than 3 hours, more preferably not more than 1 hour and most preferably not more than 30 minutes, where the periods of time specified for the minimum and maximum durations of the transition periods can be combined with one another as desired.

It is particularly preferable to conduct the reaction in the reaction space in the presence of an inert substance (4).

In the case of the liquid phase reaction, an inert substance (4) of this kind is an inert solvent. Suitable inert solvents (4) for the liquid phase phosgenation are solvents that are inert under the reaction conditions, for example monochlorobenzene, dichlorobenzene (especially the ortho isomer), trichlorobenzene, dioxane, toluene, xylene, methylene chloride, perchloroethylene, trichlorofluoromethane, chloronaphthalene, decahydronaphthalene or butyl acetate. Particular preference is given to monochlorobenzene and dichlorobenzene.

In the case of the gas phase reaction, an inert substance (4) of this kind is either an inert gas (meaning that the substance (4) is already in gaseous form at room temperature) or the vapors of an inert solvent. Suitable inert gases are, for example, nitrogen or noble gases such as helium or argon. Particular preference is given to nitrogen. Suitable solvents whose vapors can be used as inert substances (4) are, for example, aromatics such as chlorobenzene, dichlorobenzene (especially the ortho isomer), toluene, xylene or decahydronaphthalene. Particular preference is given to chlorobenzene and dichlorobenzene.

In the case of use of an inert substance (4) as diluent, it is appropriate and preferable to supply the amine (2) to the reaction space in the form of a mixture (20) with the inert substance (4) and/or the phosgene (3) to the reaction space in the form of a mixture (30) with the inert substance (4). It is possible here, in the steady states before and after the change in load, to choose the same concentrations of amine (2) in the mixture 20 and phosgene (3) in the mixture 30 as described in the prior art. Preferably, before and after a change in load, the same concentrations of amine (2) in the mixture 20 and of phosgene (3) in the mixture 30 are established.

During a Transition Period, it is Preferable that the average concentration of the amine (2) in the mixture (20) is not more than equal to the average concentration of the amine (2) in the mixture (20) during the period of production with the production capacity $m_{1,\ target}$ (A), and/or that the average concentration of the phosgene (3) in the mixture (30) during the transition period is equal to the average concentration of the phosgene (3) in the mixture (30) during the period of production with the production capacity $m_{1,\ target}$ (A).

The former preferred embodiment counteracts the formation of deposits in the reaction space, since sufficient dilution of the amine is ensured. If the latter preferred embodiment is implemented, the increase in the phosgene excess in accordance with the invention during the transition period (feature (iii-2)) has the effect that there is also increased introduction of inert material (4) into the reaction space with the phosgene/inert material stream (30), which likewise counteracts the formation of deposits in the reaction space. The positive effect occurs to the most significant degree when both embodiments are implemented in conjunction with one another. If, in the steady state, no addition of an inert substance (4) is intended, the above-described positive effect can also be effected by addition of an inert substance (4) directly to the reaction space during the transition period $t_U$, without prior mixing with $m_2$ or $m_3$. Preferably, this addition of an inert substance is effected at to or has already been effected for a while, preferably 1.0 minute to 5.0 minutes, before $t_0$, such that sufficient dilution with inert substances is assured during the critical period of the change in load.

Depending on the production rate (nameplate load, partial load or during a change in load), sufficiently rapid mixing of the reactants has to be assured. Methods of implementing short mixing times are known in principle. In the mixing devices, it is possible to use mixing aggregates having dynamic or static mixers. In liquid phase phosgenation, it is possible with preference to use dynamic mixing elements in the mixing units. Suitable dynamic mixing elements are, for example, mixing elements as described in EP 2 077 150 A1. In gas phase phosgenation, preference is given to using static mixing elements. Suitable static mixing elements are, for example, mixing elements as described in EP-A-1 526 129.

Suitable isocyanates (1) which can be prepared by the process of the invention are especially aromatic di- and polyisocyanates, for example methylene diphenyl diisocyanate (MMDI, or else diisocyanates of the diphenylmethane series) as isomers or as isomer mixture, polymethylene polyphenylene polyisocyanate (PMDI, or else isocyanates of the diphenylmethane series), mixtures of methylene diphenyl diisocyanate and polymethylene polyphenylene polyisocyanate (MDI, or else di- and polyisocyanates from the diphenylmethane series), tolylene diisocyanate (TDI) as pure isomers or isomer mixture, isomers of xylylene diisocyanate (XDI), isomers of diisocyanatobenzene, xylene 2,6- isocyanate, naphthylene 1,5-diisocyanate (1,5-NDI), diisocyanates based on aliphatic or cycloaliphatic hydrocarbons having 2 to 18 carbon atoms, for example butane 1,4-diisocyanate, pentane 1,5-diisocyanate, hexane 1,6-diisocyanate (HDI), octane 1,8-diisocyanate, nonane 1,9-diisocyanate, decane 1,10-diisocyanate, 2,2-dimethylpentane 1,5-diisocyanate, 2-methylpentane 1,5-diisocyanate (MPDI), 2,4,4(or 2,2,4)-trimethylhexane 1,6-diisocyanate (TMDI), cyclohexane 1,3- and 1,4-diisocyanate, 1-isocyanato-3,3,5-trimethyl-5-isocyanatomethylcyclohexane (IPDI), 2,4- or 2,6-diisocyanato-1-methylcyclohexane (H6-TDI), 1-isocyanato-1-methyl-4(3)-isocyanatomethylcyclohexane (AMCI), 1,3(and/or 1,4)-bis(isocyanatomethyl)cyclohexane, bis(isocyanatomethyl)norbornane (NBDI), 4,4' (and/or 2,4')-diisocyanatodicyclohexylmethane, (cyclo) aliphatic triisocyanates having up to 22 carbon atoms, for example triisocyanatocyclohexane, tris(isocyanatomethyl) cyclohexane, triisocyanatomethylcyclohexane, 1,8-diisocyanato-4-(isocyanatomethyl)octane, undecane 1,6,11-triisocyanate, 1,7-diisocyanato-4-(3-isocyanatopropyl)heptane, 1,6-diisocyanato-3-(isocyanatomethyl)hexane and 1,3,5-tris (isocyanatomethyl)cyclohexane.

The amines (2) corresponding to the above isocyanates (1) are aromatic di- and polyamines, for example methylenediphenyldiamine (MMDA, or else diamines from the diphenylmethane series) as isomers or as isomer mixture, polymethylenepolyphenylpolyamine (PMDA, or else polyamines from the diphenylmethane series), mixtures of methylenediphenyldiamine and polymethylenepolyphenylenepolyamine (MDA, or else di- and polyamines from the diphenylmethane series), tolylenediamine (TDA) as pure isomers or isomer mixture, isomers of xylylenediamine (XDA), isomers of diaminobenzene, 2,6-xylidine, naphthylene-1,5-diamine (1,5-NDA), diamines based on aliphatic or cycloaliphatic hydrocarbons having 2 to 18 carbon atoms, for example 1,4-diaminobutane, 1,5-diaminopentane, 1,6-diaminohexane (HDA), 1,8-diaminooctane, 1,9-diaminononane, 1,10-diaminodecane, 2,2-dimethyl-1,5-diaminopentane, 2-methyl-1,5-pentanediamine (MPDA), 2,4,4(or 2,2, 4)-trimethyl-1,6-diaminohexane (TMDA), 1,3- and 1,4-diaminocyclohexane, 1-amino-3,3,5-trimethyl-5-aminomethylcyclohexlmane (IPDA), 2,4- or 2,6-diamino-1-methylcyclohexane (H6-TDA), 1-amino-1-methyl-4(3)-aminomethylcyclohexane (AMCA), 1,3(and/or 1,4)-bis (aminomethyl)cyclohexane, bis(aminomethyl)norbornane (NBDA), 4,4'(and/or 2,4')-diaminodicyclohexylmethane, (cyclo)aliphatic triamines having up to 22 carbon atoms, for example triaminocyclohexane, tris(aminomethyl)cyclohexane, triaminomethylcyclohexane, 1,8-diamino-4-(aminomethyl)octane, undecane-1,6,11-triamine, 1,7-diamino-4-(3-aminopropyl)heptane, 1,6-diamino-3-(aminomethyl) hexane and 1,3,5-tris(aminomethyl)cyclohexane.

Figure 5:
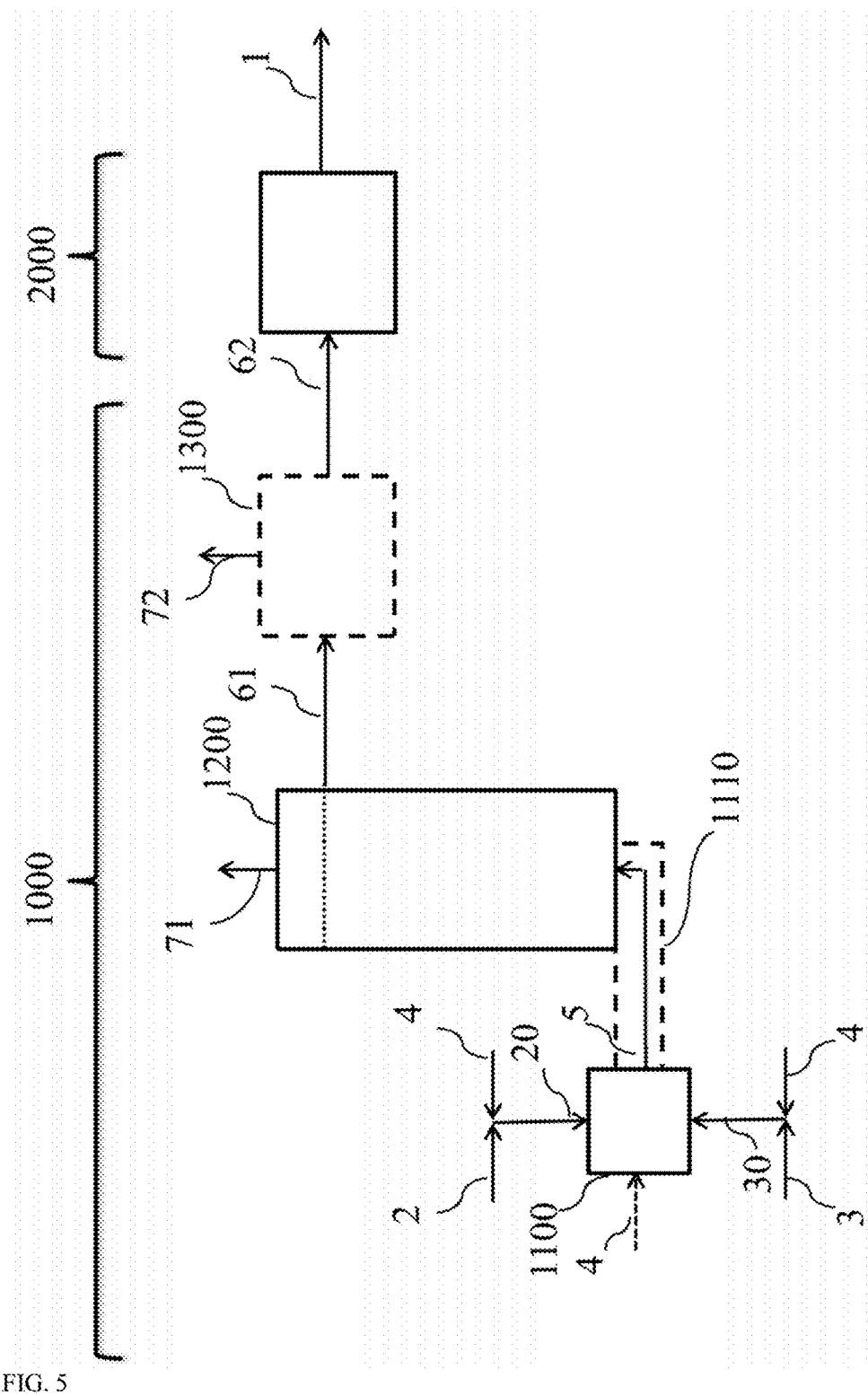
FIG. 5 illustrates a process flow for an embodiment of the invention for preparing isocyanates in the liquid phase.

In the steady state before and after the change in load, the process of the invention can be operated as known from the prior art. Preferred embodiments of liquid and gas phase phosgenation in the steady state are outlined hereinafter:

The process for preparing isocyanates (1) in the liquid phase is conducted in a production plant comprising a reaction zone and a workup zone. In this regard, see also FIG. 5. (In the passages of text which follow, the apparatuses shown in FIG. 5 are given the prefix "5-", in order to distinguish them from the apparatuses in FIG. 6 (gas phase phosgenation). In FIG. 5 itself, this prefix is dispensed with.) This process is particularly suitable for—but not limited to—the preparation of di- and polyisocyanates of the diphenylmethane series and of toluene diisocyanate, particular preference being given to the preparation of di- and polyisocyanates of the diphenylmethane series. The process preferably comprises the following steps:

I) reacting an amine (2), preferably in the form of an amine solution (20) in a solvent (4), with phosgene (3), preferably in the form of a phosgene solution (30) in a solvent (4), in the liquid phase in a reaction zone (5-1000) comprising
  I.1) a mixing device (5-1100) for mixing amine (2) or amine solution (20) with phosgene (3) or phosgene solution (30) and optionally further solvent (4),
  I.2) a reaction zone (5-1200—"phosgenation tower") arranged downstream of the mixing device in flow direction, where there may be a further dwell time device (5-1110—"suspension conduit") between 5-1100 and 5-1200, and
  I.3) optionally, an apparatus for cleavage of carbamoyl chloride (5-1300),
  wherein
  the amine (2), preferably in the form of an amine solution (20), with a mass flow $m_2$ and the phosgene (3), preferably in the form of a phosgene solution (30), with a mass flow $m_3$ and optionally solvents (4) with a mass flow $m_4$ are conducted into the mixing device 5-1100 and mixed therein, and the mixture obtained is converted further in the downstream reaction zone 5-1200 and separated into a liquid stream (61, 62) comprising crude isocyanate and solvent (and traces of phosgene and hydrogen chloride) and a gaseous stream (71, 72) comprising phosgene and hydrogen chloride (and traces of solvent);

II) to VI), preferably II) to XII), workup of the crude isocyanate in a workup zone (5-2000) to give the desired isocyanate end product (1), wherein the individual steps comprise the following:

II) separating the liquid stream (61 or 62) from step I) into a liquid stream (80) comprising solvent and crude isocyanate (and traces of phosgene), and a gaseous stream (90) comprising phosgene and hydrogen chloride (and traces of solvent) in a distillation apparatus (5-2100—"dephosgenation column");

III) separating the liquid stream (80) into a gaseous stream (110) comprising solvent (and traces of phosgene) and a liquid stream (100) comprising crude isocyanate (and traces of solvent) in a distillation apparatus (5-2200—"solvent column");

IV) separating the gaseous stream (110), preferably after it has been liquefied in a condenser (5-2310), into a liquid stream (120) comprising solvent and a gaseous stream (130) comprising phosgene in a distillation apparatus (5-2300—"solvent stripper");

V) obtaining a liquid isocyanate stream (140) from the liquid stream (100), which affords a gaseous stream (150) comprising secondary components and optionally solvent, in a distillation apparatus (5-2400), preferably comprising the removal of polymeric isocyanate fractions (141) in an upstream unit for polymer removal (5-2410—"polymer removal", PMA);

VI) absorbing the gaseous streams (71), (72), (90) and (130) in solvent (4) to obtain a liquid stream (160) comprising solvent and phosgene, and a gaseous stream (170) comprising hydrogen chloride in an absorption apparatus (5-2500—"phosgene absorber");

VII) optionally and preferably, absorbing the gaseous stream (170) in water or dilute hydrochloric acid in a further absorption apparatus (5-2600—"HCl absorption column");

VIII) optionally and preferably, cleaning offgas streams at least from VII), preferably cleaning offgas streams from all the plant sections present, in an apparatus for offgas cleaning (5-3000);

The preparation of isocyanates (1) in a steady state by this process can be summarized by way of example as follows (in this regard see also FIG. 5; the workup zone 5-2000 is shown then merely in schematic form without going into detail):

a) Core operation of step I): the amine is reacted with phosgene in a solvent to give the corresponding isocyanate. This is done in a reaction space at least comprising the mixing device 5-1100 and the reaction zone 5-1200. The crude process product obtained is separated into a liquid stream (61) comprising the crude isocyanate, optionally partly in the form of the corresponding carbonyl chloride, and solvent (and also traces of phosgene and hydrogen chloride), and a gaseous stream (71) comprising phosgene and hydrogen chloride (and also traces of solvent). If the apparatus 5-1300 is present, a liquid stream 62 (comprising the crude isocyanate and solvent (and also traces of phosgene and hydrogen chloride)) and a gaseous stream 72 (comprising predominantly hydrogen chloride and traces of phosgene) are obtained therein.

b) Core operation of step II): removal of further hydrogen chloride formed in the reaction together with converting phosgene from stream 61 (if 5-1300 is present: from stream 62) in what is called the dephosgenation column 5-2100 (not shown in FIG. 5), c) Core operation of step III): removal of solvent from the liquid stream 80 obtained in step II) in what is called the solvent column 5-2200 (not shown in FIG. 5).

d) Core operation of step IV): removal of phosgene from the gaseous stream 110 obtained in step III), preferably after liquefaction thereof in a condenser (5-2310), in what is called the solvent stripper 5-2300 (not shown in FIG. 5).

e) Core operation of step V): removal of solvent from the liquid stream 100 obtained in step III) by means of distillation (5-2400), preferably comprising the removal of polymeric isocyanate fractions (141), to obtain the isocyanate stream 140 (not shown in FIG. 5).

f) Core operation of step VI): absorption of the gaseous streams from steps I), II) and III) in a solvent in what is called the phosgene absorber 5-2500 (not shown in FIG. 5).

g) Core operation of step VII) (optional): absorption of the gas stream 170 obtained in step VI) in water or dilute hydrochloric acid in what is called the HCl absorption column 5-2600 (not shown in FIG. 5).

h) Core operation of step VIII) (optional): cleaning of the offgas streams from step VII), preferably the offgas streams from all steps, in an offgas cleaning apparatus 5-3000 (not shown in FIG. 5).

The continuous or semicontinuous, preferably continuous, production of the isocyanate in a) is effected in a reaction zone by a process known from the prior art. Suitable processes are described, for example, in EP 2 077 150 B1, EP 1 616 857 A1, EP 1 873 142 A1, EP 0 716 079 B1 or EP 0 314 985 B1. However, concentrations and flow rates of the amine and phosgene reactants are preferably chosen such that a molar ratio of phosgene to primary amino groups of 1.10:1 to 30.0:1, more preferably of 1.25:1 to 5.00:1, is established in the mixing zone. All processes for the production of an isocyanate in the liquid phase give a crude process product which is divided/separated into a liquid phase (61, 62) comprising, as well as the desired isocyanate, dissolved hydrogen chloride, excess dissolved phosgene and solvent, and a gas phase (71, 72) comprising hydrogen chloride gas, excess gaseous phosgene and gaseous solvent.

The further removal of hydrogen chloride and phosgene from the liquid crude isocyanate stream 61/62 in what is called the dephosgenation column 5-2100 in b) can be effected by any desired process known from the prior art, preferably as described in DE-A-10260084.

The further removal of solvent from the liquid isocyanate stream 80 in what is called the solvent column 5-2200 in c) can be effected by any desired process known from the prior art, preferably as described in EP 1 854 783 B1.

The removal of phosgene from the gaseous solvent stream 110 thus obtained, preferably after liquefaction thereof in a condenser (5-2310), in what is called the solvent stripper 5-2300 in d) can be effected by any desired process known from the prior art, preferably as described in EP 1 854 783 B1.

The removal of solvent from the liquid isocyanate stream 100 obtained in step III) in e), optionally comprising a polymer removal, can be effected by any desired process known from the prior art. Suitable processes are described in EP 1 854 783 A2 and EP 1 506 957 A1, or else in EP 1 371 635 B1.

The absorption of the gaseous streams from steps I), II) and III) in a solvent in what is called the phosgene absorber 5-2500 in f) can be effected by any desired process known from the prior art, preferably as described in DE-A-10260084 or EP 2 093 215 A1.

The absorption of the HCl gas stream 170 thus obtained in water or dilute hydrochloric acid in what is called the HCl absorption column 5-2600 for obtaining hydrochloric acid in g) can be effected by any desired process known from the prior art. Preference is given to procedures as described in EP 2 021 275 B1 and EP 1 743 882 B1.

The process step of process off gas treatment in h) can be effected by any process known from the prior art.

Figure 6:
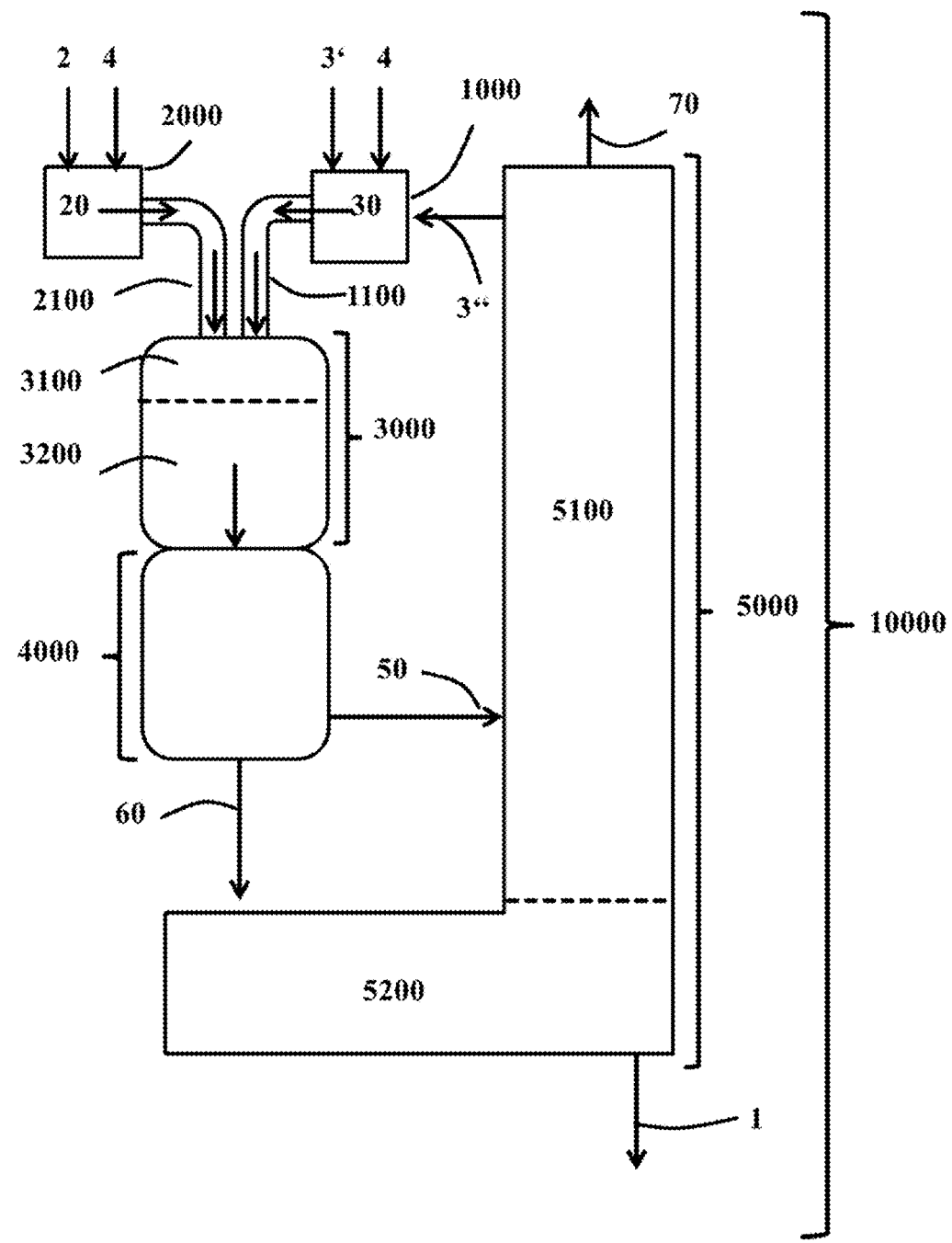
FIG. 6 illustrates a process flow for an embodiment of the invention for preparing isocyanates in the gas phase.

The process for preparing isocyanates (1) in the gas phase is conducted in a production plant (10000) (cf. FIG. 6). (In the passages of text which follow, the apparatuses shown in FIG. 6 are given the prefix "6-", in order to distinguish them from the apparatuses in FIG. 5 (liquid phase phosgenation). In FIG. 6 itself, this prefix is dispensed with.) This process is very particularly suitable for, but is not limited to, the preparation of tolylene diisocyanate. The gas phase phosgenation plant (6-10000) comprises at least (i) an apparatus 6-1000 for providing a gaseous phosgene stream, optionally comprising, as well as phosgene (3), an inert substance (4), (ii) an apparatus 6-2000 for providing a gaseous amine stream, optionally comprising, as well as amine (2), an inert substance (4), (iii) a mixing zone (6-3100) for mixing the streams of gaseous amine and gaseous phosgene, the mixing zone being connected by devices (6-1100, 6-2100) respectively to the apparatus 6-1000 and the apparatus 6-2000, (iv) a reaction zone (6-3200) arranged downstream of the mixing zone (6-3100) for further conversion of the previously mixed streams of gaseous amine and gaseous phosgene, (v) a reaction stopping zone (6-4000) arranged downstream of the reaction zone (6-3200) to end the reaction, and optionally (vi) a workup section (6-5000) comprising devices for recovery and recycling of unconverted phosgene (3") (6-5100) and devices for obtaining the isocyanate (1) prepared in pure form (6-5200).

(i) As apparatus for provision of a gaseous phosgene stream (6-1000), it is possible in principle to use any apparatus which is known from the prior art and is suitable for the conversion of phosgene to the gas phase. Preferably, the phosgene gas is generated by distillation or partial evaporation in a distillation column, as described in DE 10 2009 032413 A1 in paragraphs [0081] to [0118]. The energy can be supplied in the bottom of the column by any conceivable evaporator, for example a natural circulation evaporator, climbing film evaporator and falling film evaporator. Falling film evaporators are especially preferred. In the apparatus 6-1000, the phosgene (3) used in the phosgenation is heated to a temperature of 200° C. to 600° C., preferably of 250° C. to 420° C., more preferably of 250° C. to 400° C.

(ii) As apparatus for provision of a gaseous amine stream (6-2000), it is possible in principle to use any apparatus which is known from the prior art and is suitable for the conversion of an amine to the gas phase, such as evaporation apparatuses known to those skilled in the art. In a preferred embodiment, the apparatus 6-2000 comprises a device for evaporation and a device for subsequent superheating of the amine (2). Very particular preference is given to multistage evaporation and superheating systems in which droplet separators are installed between the evaporation and superheating systems and/or the evaporation apparatuses also have the function of a droplet separator. Suitable droplet separators are described, for example, in "Droplet Separation", A. Bürkholz, VCH Verlagsgesellschaft, Weinheim—New York—Basle—Cambridge, 1989. After leaving the last superheater in flow direction, the gaseous amine stream (20 in FIG. 6) preheated to its target temperature is fed to the reaction space. In the apparatus 6-1000, the amine (2) evaporates and is heated to a temperature of 200° C. to 600° C., preferably of 250° C. to 420° C., more preferably of 250° C. to 400° C.

(iii) A usable mixing zone (6-3100) can be constructed in a manner known to those skilled in the art, preferably as described in EP-A-2 196 455, especially in paragraphs [0047] to [0049], and EP-A-1 935 876, especially in paragraphs [0027] to [0029]. The mixing zone begins where the streams of gaseous amine and gaseous phosgene (20 and 30 respectively in FIG. 6) meet one another for the first time in regular operation.

(iv) The amine and phosgene streams that meet one another for the first time in the mixing zone (6-3100) are converted further in a delay apparatus, the reaction zone (6-3200). Mixing zone (6-3100) and reaction zone (6-3200) can preferably also be combined in a single apparatus, the reactor (6-3000), as described in EP 2 196 455 A1, especially in paragraphs [0042] to [0049].

The devices 6-1100 and 6-2100 which connect the apparatuses for provision of the gaseous phosgene gas stream (6-1000) and amine gas stream (6-2000) to the mixing zone (6-3100) are those devices which are suitable for transfer of the respective gas stream from the apparatuses 6-1000 and 6-2000 into the mixing zone (6-3100). These devices comprise, as well as pipelines for transport of the gas streams, preferably also nozzle apparatuses which assure intensive mixing of phosgene gas stream (30 in FIG. 6) and amine gas stream (20 in FIG. 6) in the mixing zone (6-3100). It is possible to inject the amine and phosgene gas streams individually into the mixing zone (6-3100). However, preference is given to an embodiment in which the pipelines of the devices 6-1100 and 6-2100 open into a common nozzle apparatus (not shown in FIG. 1). In this embodiment, one of the two gas streams, preferably the amine gas stream is supplied to the mixing zone (6-3100) via an internal nozzle arranged centrally in a preferably cylindrical vessel. The other gas stream, preferably the phosgene gas stream, is introduced via the annular space formed by the outer wall of the inner nozzle and the inner wall of the vessel. The two gas streams mix at the exit orifice of the inner nozzle (=start of the mixing zone). Such an embodiment is shown, for example, in FIG. 1 of EP-A-1 449 826 and in FIG. 1 of EP-A-1 362 847. In this case, the devices 6-1100 and 6-2100 are partly integrated into one another and into the mixing zone (6-3100). It is also possible, as shown in FIG. 2 of EP-A-1 449 826, to use an arrangement composed of several individual nozzles in place of a single central nozzle. Further usable embodiments for the devices 6-1100 and 6-2100 are described, for example, in EP-A-2 196 455, especially in paragraphs [0047] to [0048], and EP-A-1 935 876, especially in paragraphs [0027] and [0028].

(v) Usable reaction stopping zones (6-4000) are known to those skilled in the art. Preference is given to an embodiment as described in EP 1 935 875 B1, especially in paragraphs [0024] and [0025]. In the reaction stopping zone (6-4000), the gaseous crude product of the reaction comprising, as well as the diisocyanate (1), essentially also the hydrogen chloride coproduct and unconverted phosgene is cooled rapidly, preferably by injecting an inert solvent (preferably ortho-dichlorobenzene, ODB), optionally together with a portion of the previously formed and recycled isocyanate (1), into the crude product gas stream. Preferably, the crude reaction product is separated in the reaction stopping zone (6-4000) into a gaseous component (vapor, 50) and a liquid component (60).

In a particularly preferred configuration of the process, the crude product obtained in the reaction stopping zone (6-4000) is worked up in the same gas phase phosgenation plant (6-10000) in order to isolate diisocyanate (1) from the liquid mixture (60). In this case, the gas phase phosgenation plant (6-10000) additionally comprises (vi) a workup section (6-5000).

Suitable apparatuses for workup are described in WO 2011/003532, especially page 5 line 19 to page 28 line 5, and in EP 1 371 636 B1, EP 1 371 635 B1 and EP 1 413 571 B1, the whole document in each case. The workup section (6-5000) can be divided into devices for recovering and recycling unconverted phosgene (and for removing the hydrogen chloride coproduct) (6-5100) and devices for obtaining the isocyanate prepared in pure form (and optionally for recycling inert solvent) (6-5200). The workup section is indicated merely schematically in FIG. 6 without the details given hereinafter. More particularly, the workup section (6-5000) comprises a scrubbing column (6-5110) for removing isocyanate from the vapors (50) from the reaction stopping zone (6-4000) by scrubbing with an inert solvent, a phosgene absorption column (6-5120) for recovering phosgene from the vapors from the scrubbing column (6-5110) by absorption in an inert solvent, which results in separation of hydrogen chloride and inerts (70) from the phosgene, a phosgene desorption column (6-5130) for separation of phosgene and inert solvent, a solvent column (6-5210), especially for removal of low boilers (especially inert solvent from the reaction stopping zone) from the crude isocyanate, a fine purification column (6-5220), especially for removal of high boilers (e.g. polyurea-containing residues) from the isocyanate prepurified in the solvent column, such that purified end product is obtained.

The phosgene (3) required for the two process regimes, liquid and gas phase phosgenation, can in principle be prepared by all processes known from the prior art. For this purpose, it is possible to utilize a "low-temperature combiner" according to EP 1 640 341 B1 or a "high-temperature combiner" according to EP 0 134 506 B1. High-temperature combination (see EP 0 134 506 B1)—which is used with preference—involves converting phosgene by reaction of chlorine with carbon monoxide in tubular reactors containing activated carbon as catalyst with simultaneous exploitation of the heat of reaction obtained for generation of steam. This is done by reacting, in a first tubular reactor containing granular activated carbon and having a clear tubular diameter of not more than 100 mm, 95% by volume to 98% by volume of the chlorine used with excess carbon monoxide to give phosgene at reaction temperatures exceeding 250° C. The heat of reaction obtained here is removed by evaporative cooling of a liquid that boils at 150° C. to 320° C. or with a non-boiling liquid, the temperature of which is kept at 150° C. to 320° C. at the reactor outlet by means of forced circulation pumps and temperature control. The liquid or vaporous heat carrier leaving the reactor is condensed in a heat exchanger charged with water as cooling medium to generate steam and/or cooled to a temperature below the temperature of the heat carrier at the reactor exit and recycled into the reactor. The reaction gases leaving the reactor are cooled to a temperature of 50° C. to 120° C. and then passed into a second reactor containing granular activated carbon, the temperature of which is set to 50° C. to 100° C. by thermostatic means and in which the conversion is conducted to completion, such that the phosgene leaving the second reactor has a residual chlorine content of less than 50 ppmv. The phosgene exiting at the top of the reactor is condensed as described above.

The procedure of the invention gives rise to the following advantages for the preparation of isocyanates (1):
i) The productivity of the phosgenation plant is higher because fewer purification periods are needed, particularly for the reaction zone and the downstream plant segments.
ii) The productivity of the phosgenation plant is higher because fewer pressure drops occur in the mixing apparatuses and pipelines in the reaction zone.
iii) The energy efficiency of the reaction section is higher because fewer deposits on the apparatus walls assure better heat transfer.
iv) A lower level of waste arises after the cleaning of the reaction section and downstream plant segments (minimized polyurea formation).
v) The formation of solids which can impair the downstream apparatuses such as pumps and columns by abrasion or deposits is minimized.
vi) Lower specific and possibly absolute phosgene holdup.
vii) Saving of energy for the workup of the solvent in the liquid phase.
viii) Saving of energy for the recycling of phosgene.
ix) Reduction in the thermal stress on the crude isocyanate.

Thus, the procedure of the invention, during a non-steady state (during a transition period), enables a technically seamless change of load without subsequent outage periods in the steady state that follows with constantly high quality of the desired isocyanate end product. The process of the invention also enables a rapid change of load and hence rapid reaction to events such as raw material shortages, etc.

The present invention is further elucidated by the drawings and examples which follow, but without being limited thereto.

The examples show:

FIG. 1-4 the plot of the mass flow rates of phosgene (3) and amine (2) against time in the process of the invention over the transition period.

The figures each show the plot of the mass flow rates of amine and phosgene against time in various embodiments of the process of the invention. Plotted on the x axis in each case is the time t, where the time until $t_0$ and after $t_1$ describe the respective steady plant states, and plotted on the y axis in each case are the mass flow rates $m_2$ and $m_3$. Until the point in time $t_0$ is reached, the mass flow rates for amine ($m_2$, identified in the figure as "A") and phosgene ($m_3$, identified in the figure as "P") are constant in the phosgenation reactor, referred to as reaction space in the terminology of the present invention.

Figure 2:
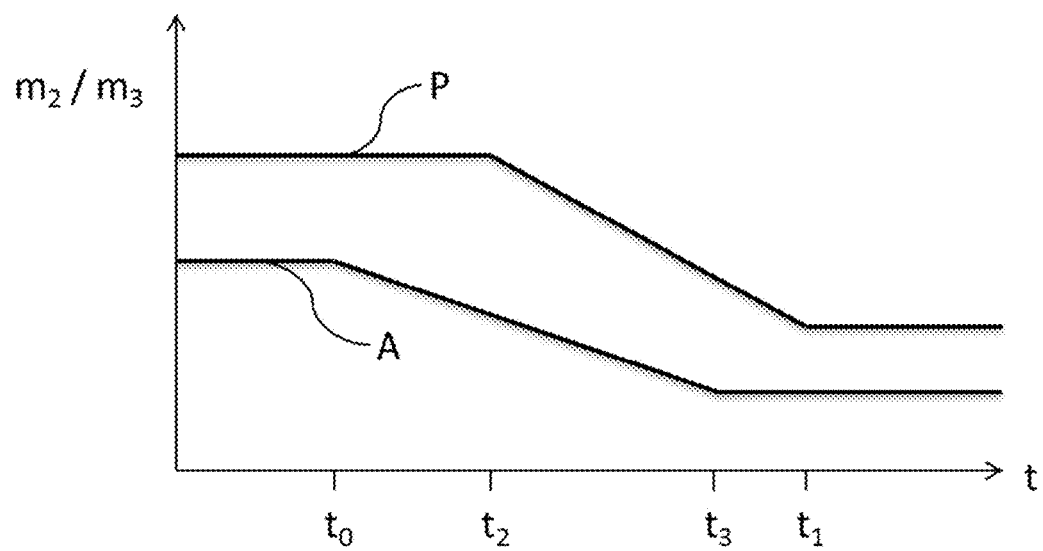
FIG. 2 is a graph of the mass flow rates of phosgene and amine against time in the process of the invention over the transition period in which the production capacity is being reduced.

FIG. 1: It is decided that the production capacity is to be reduced. For this purpose, with an unchanged level of the mass flow rate of phosgene, beginning at the point in time $t_0$, the mass flow rate of amine into the reaction space is reduced until it reaches the desired target value $m_{2,\ target}$ (E) at the point in time $t_1$.

At the point in time $t_2$, reduction in the mass flow rate of phosgene into the reaction space is commenced until it likewise reaches the desired target value ($m_{3,\ target}$ (E)) at the point in time $t_1$. It is apparent that the instantaneous phosgene excess at $t_2$ is greater than before to (feature (iii-1)) and that the average phosgene excess during the transition period is greater than the phosgene excess before $t_0$ (feature (iii-2)).

After the time $t_1$, once the desired steady state has been attained, the mass flow rates for amine ($m_2$, identified in the figure as "A") and for phosgene ($m_3$, identified in the figure as "P") into the phosgenation reactor, referred to as reaction space in the terminology of the present invention, are constant again, and the mass flow rate of phosgene relative to amine is less than before the point in time $t_0$ (naturally with observation of feature (ii)). The mass flow rates of phosgene and amine reach the desired steady state at the same time.

In the non-steady state between $t_0$ and $t_1$, the change in the addition of phosgene and amine can run not only in a linear manner but also in a non-linear manner with a curved profile, given compliance with the other requirements of the invention.

FIG. 2: It is decided that the production capacity is to be reduced. For this purpose, with an unchanged level of the mass flow rate of phosgene, at the point in time $t_0$, the mass flow rate of amine into the reaction space is reduced until it reaches the desired target value $m_{2,\ target}$ (E) at the point in time $t_3$.

At the point in time $t_2$, reduction in the mass flow rate of phosgene into the reaction space is commenced until it likewise reaches the desired target value ($m_{3,\ target}$ (E)) at the point in time $t_1$. It is apparent that the instantaneous phosgene excess at $t_2$ is greater than before to (feature (iii-1)) and that the average phosgene excess during the transition period is greater than the phosgene excess before to (feature (iii-2)).

After the time $t_1$, once the desired steady state has been attained, the mass flow rates for amine ($m_2$, identified in the figure as "A") and phosgene ($m_3$, identified in the figure as "P") are constant again in the phosgenation reactor, referred to as reaction space in the terminology of the present invention. The mass flow rates of phosgene and amine do not reach the desired steady state at the same time. The mass flow rate of amine is constant again at an earlier point in time ($t_3$) than that of phosgene, such that, at the point in time $t_3$, the desired production capacity has been attained again, but the phosgene mass flow rate $m_3$ is reduced further between $t_3$ and $t_2$ until, ultimately, the two mass flow rates are in the steady state at $t_1$.

In the non-steady state between to and $t_1$, the change in the addition of phosgene and amine can run not only in a linear manner but also in a non-linear manner with a curved profile, given compliance with the other requirements of the invention.

Figure 3:
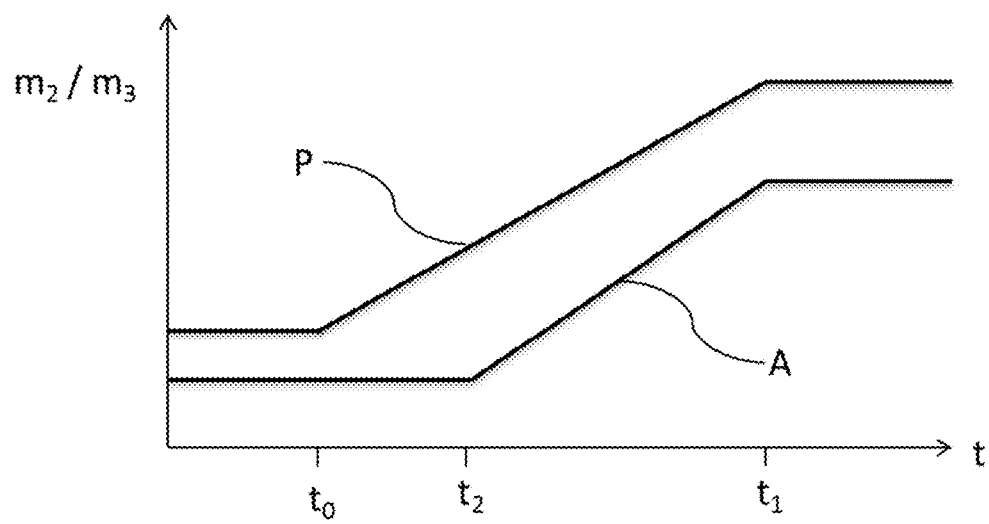
FIG. 3 is a graph of the mass flow rates of phosgene and amine against time in the process of the invention over the transition period in which the production capacity is being increased.

FIG. 3: It is decided that the production capacity is to be increased. For this purpose, with an unchanged level of the mass flow rate of amine, at the point in time $t_0$, the mass flow rate of phosgene into the reaction space is increased until it reaches the desired target value ($m_{3,\ target}$ (E)) at the point in time $t_1$.

At the point in time $t_2$, increasing of the mass flow rate of amine into the reaction space is commenced until it likewise reaches the desired target value ($m_{2,\ target}$ (E)) at the point in time $t_1$. It is apparent that the instantaneous phosgene excess at $t_2$ is greater than before to (feature (iii-1)) and that the average phosgene excess during the transition period is greater than the phosgene excess before to (feature (iii-2)).

After the time $t_1$, once the desired steady state has been attained, the mass flow rates for amine ($m_2$, identified in the figure as "A") and phosgene ($m_3$, identified in the figure as "P") are constant again in the phosgenation reactor, referred to as reaction space in the terminology of the present invention. The mass flow rates of phosgene and amine reach the desired steady state and hence the desired production capacity at the same time.

In the non-steady state between $t_0$ and $t_1$, the change in the addition of phosgene and amine can run not only in a linear manner but also in a non-linear manner with a curved profile, given compliance with the other requirements of the invention.

Figure 4:
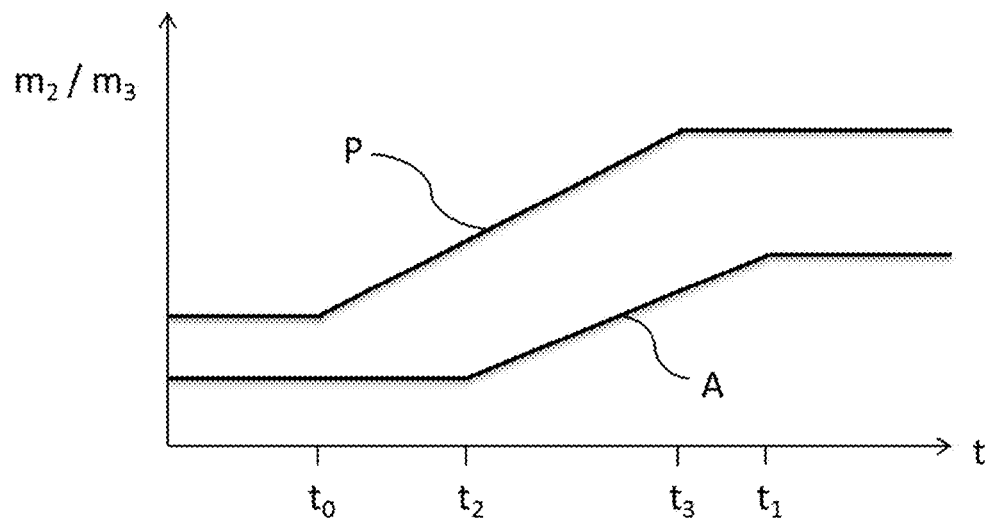
FIG. 4 is a graph of the mass flow rates of phosgene and amine against time in the process of the invention over the transition period in which the production capacity is being increased.

FIG. 4: It is decided that the production capacity is to be increased. For this purpose, with an unchanged level of the mass flow rate of amine, at the point in time $t_0$, the mass flow rate of phosgene into the phosgenation reactor is increased until it reaches the desired target value ($m_{3,\ target}$ (E)) at the point in time $t_3$.

At the point in time $t_2$, increasing of the mass flow rate of amine into the reaction space is commenced until it likewise reaches the desired target value ($m_{2,\ target}$ (E)) at the point in time $t_1$. It is apparent that the instantaneous phosgene excess at $t_2$ is greater than before to (feature (iii-1)) and that the average phosgene excess during the transition period is greater than the phosgene excess before $t_0$ (feature (iii-2)).

After the time $t_1$, once the desired steady state has been attained, the mass flow rates for amine ($m_2$, identified in the figure as "A") and phosgene ($m_3$, identified in the figure as "P") are constant again in the phosgenation reactor, referred to as reaction space in the terminology of the present invention. The mass flow rates of phosgene and amine do not reach the desired steady state at the same time. The mass flow rate of phosgene is constant again at an earlier point in time ($t_3$) than that of amine, and so the desired production capacity has not been attained yet at the point in time $t_3$. In the period between $t_3$ and $t_1$, the amine mass flow rate continues to be increased until, at $t_1$, both mass flow rates are in the steady state. Only now is the desired production capacity attained.

In the non-steady state between $t_0$ and $t_1$, the change in the addition of phosgene and amine can run not only in a linear manner, given compliance with the other requirements of the invention.

EXAMPLES

General Conditions for the Preparation of a Mixture of Methylene Diphenyl Diisocyanate and Polyethylene Polyphenylene Polyisocyanate (Collectively MDI hereinafter) in the Steady State; Cf. Also FIG. 5

4.3 t/h of a mixture of methylenediphenyldiamine and polymethylenepolyphenylenepolyamine (collectively MDA hereinafter; 2) at a temperature of 110° C. are mixed with 11 t/h of monochlorobenzene (MCB; 4) at a temperature of 30° C. as solvent by means of a static mixer (5-1100) to give a 28% MDA solution (20). Phosgene (3) is provided by means of a phosgene generator and a phosgene liquefier. Thereafter, the phosgene (3) is diluted to a 35% phosgene solution (30) with MCB (4) in a phosgene dissolution tank. 24 tonnes per hour of 35% phosgene solution (30) at a temperature of 0° C. are reacted with 4.3 tonnes per hour of MDA (2) in the form of the 28% MDA solution (20) at a temperature of 45° C. in an adiabatic reaction, as described in EP 1 873 142 B1. After the two raw material solutions have been mixed in the mixing apparatus (5-1100), the reaction solution (5) obtained is run at a temperature of 85° C. through a suspension conduit (5-1110) into a heated phosgenation tower (5-1200). At the top of the phosgenation tower, the absolute pressure is 1.6 bar and the temperature is 111° C. The hydrogen chloride formed in the reaction is removed together with traces of phosgene and MCB as gas stream (71). The liquid reaction mixture (61) is withdrawn from the phosgenation tower (5-1200) and fed to the workup sequence (5-2000). For this purpose, it is first introduced as a sidestream into a heated dephosgenation column. At a top temperature of 116° C. and an absolute pressure of 1.6 bar, phosgene is removed overhead together with traces of MCB and hydrogen chloride. Phosgene is absorbed in a phosgene absorption column and run into the phosgene dissolution tank, and hydrogen chloride is directed into a hydrogen chloride absorber and then into a hydrochloric acid tank for further use. After removal of hydrogen chloride and excess phosgene from the isocyanate-containing reaction solution, a crude isocyanate solution is obtained, which is discharged from the bottom of the dephosgenation column and run at a temperature of 155° C. into a first distillation stage, in order to free it of the MCB solvent. The absolute pressure at the top of this solvent distillation column is 800 mbar at a bottom temperature of 155° C. MCB is drawn off in gaseous form overhead, this MCB gas stream being sprayed with cold MCB (30° C.) in a scrubbing column, in order to prevent any possible entrainment of isocyanate into the vacuum conduits. The reaction product is discharged from the bottom of the column and freed of residual MCB down to 1% in a second column. Subsequently, in a countercurrent evaporator, at an absolute pressure of 20 mbar and a bottom temperature of 210° C., the product is freed of secondary components such as phenyl isocyanate and residual MCB. This affords 5.4 t/h of MDI as bottom product, which is worked up by means of further distillation to give MDI of the desired purity (1) and then run into a tank for further use.

MDI prepared in this way has a residual solvent content of MCB of <5 ppm (GC), a content of readily hydrolyzable chlorine (also referred to as acidity) of <100 ppm (acidimetric titration by Bayer analysis method 2011-0461102-96) and a content of chemically bound chlorine of <2000 ppm (Wickboldt combustion).

Example 1 (Comparative Example, Lowering the Production Capacity from Nameplate Capacity to 50% of the Nameplate Capacity)

In this example, the feed of phosgene is reduced before the feed of amine, as a result of which the phosgene excess is lowered and the concentration of the amine in the reaction mixture is increased in the transition period by comparison with the steady state of nameplate capacity (i.e. the mass of solvent relative to the total mass of the reaction mixture is lowered).

The preparation of 5.4 t/h of MDI in continuous mode was conducted at nameplate capacity as described in the general conditions. In order to bring the phosgenation plant to half-load, the phosgene solution feed was reduced 10 seconds before the MDA solution feed and the two streams were run down continuously to 50% of nameplate capacity within 40 minutes. On attainment of half-load, 2.15 t/h of MDA as a 28% solution in monochlorobenzene and 12 t/h of 35% phosgene solution were run into the mixer. Workup and distillation of the crude isocyanate left 2.7 t/h of pure MDI. After five hours of continuous operation at half-load, the phosgenation plant had to be shut down completely because the distributor trays of the dephosgenation column began to become blocked, and the pressure drop over the column rose as a result. The plant had to be shut down in order to free the dephosgenation column of baked-on urea and loose urea present in the column before it was possible to start the plant up again.

Example 2 (Inventive, Lowering the Production Capacity from Nameplate Capacity to 50% of the Nameplate Capacity)

In this example, the amine flow rate is first reduced and then, with a time delay, the phosgene flow rate is reduced, with an elevated phosgene excess and a reduced amine concentration (i.e. an elevated mass of solvent relative to the total mass of the reaction mixture) until attainment of "half-load operation". After attainment of "half-load", the phosgene excess and the amine concentration are at the same level as before in the steady state of nameplate capacity. Subsequently, the plant is run back up to nameplate capacity, with an elevated phosgene excess and a reduced amine concentration (i.e. an elevated mass of solvent relative to the total mass of the reaction mixture) until attainment of nameplate capacity. After attainment of nameplate capacity, the phosgene excess and the amine concentration are at the same level as before in the steady state of half-load operation.

The preparation of 5.4 t/h of MDI in continuous mode was conducted at nameplate capacity as described in the general conditions. Owing to shortage of raw material, the production plan had to be corrected. For this purpose, the phosgene generator was run down to the required amount of phosgene. One minute later, the phosgenation plant was run down to half-load by first reducing the MDA supply. The phosgene supply to the mixing apparatus continued to run at the prior nameplate capacity volume for one minute. Subsequently, the phosgene supply was likewise run down and, after 41 minutes, the two flow rates had been brought continuously to a production capacity of 50% of nameplate capacity (half-load), corresponding to 2.15 t/h of MDA as a 28% solution in monochlorobenzene and 12 t/h of 35% phosgene solution in monochlorobenzene. This corresponded to a production output of 2.7 t/h (MDI). The plant was run from the stocks of raw material in the tank farm until the shortage of raw material ended. The shortage of raw material was remedied after three days and it was possible to bring the plant back to nameplate capacity by first increasing the phosgene supply and then, after 1 minute, increasing the amine supply. After 41 minutes, the two flow rates had been brought continuously to nameplate capacity. Subsequently, the phosgenation plant was operated for several months as described in the general conditions. There were no problems with caking or precipitates. Over the whole period before, during and after the half-load and in the two transition phases, on-spec material was produced.

As the examples show, in the case of an improper change of load, precipitates arise immediately in the phosgenation plant for the liquid phase phosgenation. In the case of the inventive procedure in the running of the phosgenation down and up, by contrast, the formation of baked-on material and precipitates is distinctly reduced, the plant can be operated over a long production cycle, even after several changes of load, and on-spec material is produced over the whole period.

General Conditions for the Preparation of TDI in the Steady State; cf. also FIG. 6

TDA (2) is evaporated continuously in an amine evaporator (6-2000) together with nitrogen (4). The amine gas stream (20) thus obtained, containing 12 t/h of gaseous TDA (2), is injected continuously into the phosgenation reactor (6-3000) via a conduit (2100) with an amine nozzle present at the end thereof toward the phosgenation reactor (6-3000). The dwell time of the TDA stream (20) from departure from the evaporator (6-2000) until exit from the amine nozzle is 5 seconds. At the same time, via a phosgene rectifier which is used as disclosed in EP-A-1 362 847, 61 t/h of a gaseous phosgene stream are injected continuously into the phosgenation reactor (6-3000). The phosgene used is a mixture of fresh phosgene (3') and phosgene (3") recovered in the workup section (6-5000). In this case, the two reactants are mixed well, and there is no backmixing. The temperature of the gaseous TDA stream (20) at the mouth of the nozzle is 380° C. (TDA has a dwell time of about 1 second at this temperature in the feed to the nozzle mouth). The gaseous phosgene (30) has a temperature of 320° C. when it leaves the phosgene rectifier, the dwell time of the hot phosgene between the last phosgene superheater and phosgene rectifier being 2 seconds. The mixture of the gaseous amine stream and the gaseous phosgene stream has a dwell time of 8 seconds in the gas phase reactor (6-3000) and reacts at an absolute pressure of 1692 mbar to give gaseous reaction mixture. The downstream reaction stopping zone (6-4000) comprises a two-stage "quench" in which the gaseous reaction mixture is cooled down to 168° C. by spraying in ortho-dichlorobenzene (ODB), such that it is condensed and a mixture (60) of crude TDI and ODB collects in the bottoms vessel (6-4100). Excess phosgene, hydrogen chloride formed in the reaction and inerts are very substantially degassed from the bottoms vessel (6-4100) under these conditions, with reduction of the entrainment of TDI by means of internals. This residual process gas stream (50) is worked up (6-5100) to recover entrained TDI, phosgene and hydrogen chloride, as described in WO 2011/003532, page 11 lines 24 to 25. The mixture (60) from the bottoms vessel (6-4100) is worked up (6-5200) as described in EP 1 413 571 B1, giving TDI (1) in a mass flow rate of 15.6 t/h.

TDI (1) prepared in this way typically has a purity of >99.97% (gas chromatography, GC), a residual solvent content of ODB of <5 ppm (GC), a residual chlorine content of hydrolyzable chlorine of <10 ppm (titration in accordance with ASTM D4663), an acidity of bound chlorine of <5 ppm (titration in accordance with ASTM D5629), and the color number, measured as the Hazen number, is <15 (determined in accordance with DIN EN ISO 6271).

Example 3 (Comparative Example, Lowering the Production Capacity from Nameplate Capacity to 50% of the Nameplate Capacity)

In this example, the feed of phosgene is reduced before the feed of amine, as a result of which the phosgene excess is lowered and the concentration of the amine in the reaction mixture is increased in the transition period by comparison with the steady state of nameplate capacity (i.e. the mass of solvent relative to the total mass of the reaction mixture is lowered).

The gas phase plant (6-10000) is operated at a production capacity of 15.6 t/h of TDI at nameplate capacity as described in the general conditions for preparation of TDI and then run down to half load as follows: in order to bring the phosgenation plant to half-load, the phosgene solution feed was reduced 10 seconds before the MDA solution feed and the two streams were run down continuously to 50% of nameplate capacity within 40 minutes.

The phosgene generator is run down to the required amount of phosgene. One minute later, the phosgene feed to the phosgenation reactor (6-3000) is reduced and, a further 10 seconds later, the amine feed is reduced. Subsequently, the two flow rates are run down continuously to 50% of nameplate capacity within 25 minutes. The amine gas stream now contains 6 t/h of gaseous TDA. The dwell time of the TDA stream (20) from departure from the evaporator (6-2000) until exit from the amine nozzle is 10 seconds. Via the phosgene rectifier, 30.5 t/h of a gaseous phosgene stream are injected into the phosgenation reactor, where the dwell time of the hot phosgene between the last phosgene superheater and phosgene rectifier is 4 seconds. Workup and distillation of the crude isocyanate leaves 7.8 t/h of pure TDI. After 2 days, the plant has to be shut down because the pressure differential from entry of the TDA gas stream and phosgene gas stream reactants into the phosgenation reactor (6-3000) through the vapor gas exit at the bottom of the reaction stopping zone (6-4000) up to the TDI scrubbing column (6-5110) rises to 823 mbar over time, rather than 10 mbar in standard operation, and the energy required to evaporate phosgene and TDA and transfer the amine and phosgene gas streams into the phosgenation reactor (6-3000) can barely be raised (the boiling temperature of TDA (2) limits the evaporator capacity with increasing pressure). After shutdown and opening of the plant, severe polyurea-containing deposits are found at the exit of the amine nozzle, along the surface of the reactor space and on the surfaces of the quenches. The plant is cleaned over several days before it can be run up again.

Example 4 (Inventive, Lowering the Production Capacity from Nameplate Capacity to 50% of the Nameplate Capacity)

In this example, the amine stream is first reduced and then, with a time delay, the phosgene stream is reduced. In this case, there is an elevated phosgene excess and a reduced amine concentration (i.e. an elevated mass of solvent relative to the total mass of the reaction mixture) until attainment of half-load mode. After attainment of half-load, the phosgene excess and the amine concentration are at the same level as before in the steady state of nameplate capacity. Subsequently, the plant is run back up to nameplate capacity, with an elevated phosgene excess and a reduced amine concentration (i.e. an elevated mass of solvent relative to the total mass of the reaction mixture) until attainment of nameplate capacity. After attainment of nameplate capacity, the phosgene excess and the amine concentration are at the same level as before in the steady state of half-load operation.

The gas phase plant (6-10000) is operated at a production capacity of 15.6 t/h of TDI at nameplate capacity as described in the general conditions for preparation of TDI and then run down to half load, operated at half load for 7 days and then run back up to nameplate capacity as follows:

Owing to shortage of raw material, the production plan had to be corrected. Firstly, the phosgene generator is run down to the required amount of phosgene. The gas phase plant is run down to half load by, one minute later, reducing the TDA feed to the phosgenation reactor (6-3000) and, a further minute later, reducing the phosgene feed to the phosgenation reactor and then running both streams continuously down to 50% of nameplate capacity within 25 minutes. The amine gas stream now contains 6 t/h of gaseous TDA. The dwell time of the TDA stream (20) from departure from the evaporator (6-2000) until exit from the amine nozzle is 10 seconds. Via the phosgene rectifier, 30.5 t/h of a gaseous phosgene stream are injected continuously into the phosgenation reactor, where the dwell time of the hot phosgene between the last phosgene superheater and the phosgene rectifier is 4 seconds. Workup and distillation of the crude isocyanate leaves 7.8 t/h of pure TDI. The gas phase plant is run from the stocks of raw material in the tank farm until the shortage of raw material ended. After 7 days, the plant can be brought back to nameplate capacity. For this purpose, firstly, the phosgene generator is run up to the required amount of phosgene. Nameplate capacity is attained by firstly increasing the phosgene feed by raising the 30.5 t/h of a gaseous phosgene stream from half-load mode up to 61 t/h via the phosgene rectifier. 1 minute after increasing the phosgene feed, the amine feed is increased. After 25 minutes, the two flow rates have been brought continuously to nameplate capacity. Subsequently, the phosgenation plant is operated for several months as described in the general conditions. There are no problems with caking or precipitates. Over the whole period before, during and after the half-load and in the two transition phases, on-spec material has been produced. As shown by the examples, in the event of an improper change of load, there is immediate occurrence of caking in the amine nozzle, in the phosgenation reactor and on the surfaces of the quenches of the gas phase phosgenation. In the case of the inventive procedure in the running of the phosgenation up and down, by contrast, the formation of caking and precipitates is distinctly reduced. The plant can be operated over a long production cycle, even after several changes of load, and on-spec product is produced over the whole period.

The invention claimed is:
1. A continuous process for preparing an isocyanate in a production plant with a target production capacity of isocyanate, comprising reacting the amine corresponding to the isocyanate with phosgene in a reaction space, wherein
   (i) the amine is fed to the reaction space and phosgene is fed to the reaction space,
   (ii) the mass flow rate of amine fed to the reaction space and the mass flow rate of phosgene fed to the reaction space are always chosen such that phosgene is present in excess relative to the primary amino groups of the amine, and
   (iii) the target production capacity of isocyanate is changed at least once from a starting state of the operating production plant having a corresponding starting state amine mass flow rate and a starting state phosgene mass flow rate
   via a transition period
   to a final state of the operating production plant having a corresponding final state amine mass flow rate of and a final state phosgene mass flow rate, wherein during the transition period the mass flow rate of amine fed to the reaction space and the mass flow rate of phosgene fed to the reaction space are altered so that:

(iii-1) the instantaneous phosgene excess at the point in time in the transition period at which the alteration of the amine mass flow rate from the starting state amine mass flow rate to the final state amine mass flow rate is commenced is at least as high as the phosgene excess during the period of production during the starting state of the operating production plant prior to commencement of the transition period, and (iii-2) the average phosgene excess during the transition period is greater than the phosgene excess during the period of production prior to commencement of the transition period.

2. The process as claimed in claim 1, in which the target production capacity of isocyanate prior to commencement of the transition period is greater than the target production capacity of isocyanate after the end of the transition period, and in which the reduction in the amine mass flow rate fed to the reaction space is commenced prior to the reduction of the phosgene mass flow rate fed to the reaction space.

3. The process as claimed in claim 2, in which the mass flow rate of amine fed to the reaction space and the mass flow rate of phosgene to the reaction space are altered in the transition period such that they simultaneously attain the final state amine mass flow rate and the final state phosgene mass flow rate.

4. The process as claimed in claim 2, in which the mass flow rate of amine fed to the reaction space and the mass flow rate of phosgene to the reaction space are altered in the transition period such that the mass flow rate of amine fed to the reaction space attains the final state amine mass flow rate before the mass flow rate of phosgene to the reaction space attains the final state phosgene mass flow rate.

5. The process as claimed in claim 1, in which the target production capacity of isocyanate prior to commencement of the transition period is less than the target production capacity of isocyanate after the end of the transition period, and in which the increase in the amine mass flow rate fed to the reaction space is commenced after the increase in the phosgene mass flow rate fed to the reaction space.

6. The process as claimed in claim 5, in which the mass flow rate of amine fed to the reaction space and the mass flow rate of phosgene to the reaction space are altered in the transition period such that they simultaneously attain the final state amine mass flow rate and the final state phosgene mass flow rate.

7. The process as claimed in claim 5, in which the mass flow rate of amine fed to the reaction space and the mass flow rate of phosgene fed to the reaction space are altered in the transition period such that the mass flow rate of amine fed to the reaction space attains the final state amine mass flow rate after the mass flow rate of phosgene fed to the reaction space attains the final state phosgene mass flow rate.

8. The process as claimed in claim 1, in which the phosgene excess during the production at the production capacity prior to commencement of the transition period is equal to the phosgene excess during the production at the production capacity after the end of the transition period.

9. The process as claimed in claim 1, in which the reaction takes place in the presence of an inert substance.

10. The process as claimed in claim 9, in which the amine is fed to the reaction space together with the inert substance, and/or in which the phosgene is fed to the reaction space together with the inert substance.

11. The process as claimed in claim 10, in which the average concentration of the amine in the mixture during the transition period is not more than the average concentration of the amine in the mixture during the period of production at the target production capacity of isocyanate prior to commencement of the transition period, and/or in which the average concentration of the phosgene in the mixture during the transition period is equal to the average concentration of the phosgene in the mixture during the period of production at the target production capacity of isocyanate prior to commencement of the transition period.

12. The process as claimed in claim 10, in which the concentration of amine in the mixture and the concentration of phosgene in the mixture is the same in each case after the end of the transition period as they were prior to the commencement of the transition period.

13. The process as claimed in claim 1, in which the reaction of the amine with phosgene takes place in the liquid phase, and in which the inert substance, if present, is an inert solvent, and wherein the isocyanate comprises at least one of the di- and polyisocyanates of the diphenylmethane series, tolylene diisocyanate, xylylene diisocyanate, diisocyanatobenzene, xylene 2,6-isocyanate, naphthylene 1,5-diisocyanate, diisocyanates based on aliphatic or cycloaliphatic hydrocarbons having 2 to 18 carbon atoms, such as, more particularly, butane 1,4-diisocyanate, pentane 1,5-diisocyanate, hexane 1,6-diisocyanate, octane 1,8-diisocyanate, nonane 1,9-diisocyanate, decane 1,10-diisocyanate, 2,2-dimethylpentane 1,5-diisocyanate, 2-methyl-1,5-pentane diisocyanate (MPDI), 2,4,4(or 2,2,4)-trimethylhexane 1,6-diisocyanate, cyclohexane 1,3- and 1,4-diisocyanate, 1-isocyanato-3,3,5-trimethyl-5-isocyanatomethylcyclohexane, 2,4- or 2,6-diisocyanato-1-methylcyclohexane, 1-isocyanato-1-methyl-4(3)-isocyanatomethylcyclohexane, 1,3 (and/or 1,4)-bis(isocyanatomethyl)cyclohexane, bis(isocyanatomethyl)norbornane and 4,4'(and/or 2,4')-diisocyanatodicyclohexylmethane and (cyclo)aliphatic triisocyanates having up to 22 carbon atoms, such as, more particularly, triisocyanatocyclohexane, tris(isocyanatomethyl)cyclohexane, triisocyanatomethylcyclohexane, 1,8-diisocyanato-4-(isocyanatomethyl)octane, undecane 1,6,11-triisocyanate, 1,7-diisocyanato-4-(3-isocyanatopropyl)heptane, 1,6-diisocyanato-3-(isocyanatomethyl)hexane and 1,3,5-tris(isocyanatomethyl)cyclohexane.

14. The process as claimed in claim 1, in which the reaction of the amine with phosgene takes place in the gas phase, and in which the inert substance, if present, is an inert gas, and wherein the isocyanate comprises at least one of the diisocyanates of the diphenylmethane series, tolylene diisocyanate, xylylene diisocyanate, diisocyanatobenzene, xylene 2,6-isocyanate, naphthylene 1,5-diisocyanate, diisocyanates based on aliphatic or cycloaliphatic hydrocarbons having 2 to 18 carbon atoms, such as, more particularly, butane 1,4-diisocyanate, pentane 1,5-diisocyanate, hexane 1,6-diisocyanate, octane 1,8-diisocyanate, nonane 1,9-diisocyanate, decane 1,10-diisocyanate, 2,2-dimethylpentane 1,5-diisocyanate, 2-methyl-1,5-pentane diisocyanate (MPDI), 2,4,4(or 2,2,4)-trimethylhexane 1,6-diisocyanate, cyclohexane 1,3- and 1,4-diisocyanate, 1-isocyanato-3,3,5-trimethyl-5-isocyanatomethylcyclohexane, 2,4- or 2,6-diisocyanato-1-methylcyclohexane, 1-isocyanato-1-methyl-4(3)-isocyanatomethylcyclohexane, 1,3(and/or 1,4)-bis(isocyanatomethyl)cyclohexane, bis(isocyanatomethyl)norbornane and 4,4'(and/or 2,4')-diisocyanatodicyclohexylmethane
and
(cyclo)aliphatic triisocyanates having up to 22 carbon atoms, such as, more particularly, triisocyanatocyclohexane, tris(isocyanatomethyl)cyclohexane, triisocyanatomethylcyclohexane, 1,8-diisocyanato-4-(isocyanatomethyl)octane, undecane 1,6,11-triisocyanate, 1,7-diisocyanato-4-(3-isocyanatopropyl)heptane, 1,6-diisocyanato-3-(isocyanatomethyl)hexane and 1,3,5-tris(isocyanatomethyl)cyclohexane.

15. The process as claimed in claim 1, in which the target production capacity after the end of the transition period is 10% to 90% different than the target production capacity of isocyanate prior to commencement of the transition period.

16. The process as claimed in claim 1, in which the transition period has a duration of at least 0.50 minute to 3 hours.

* * * * *